US012690942B2

(12) United States Patent
Auber et al.

(10) Patent No.: US 12,690,942 B2
(45) Date of Patent: Jul. 28, 2026

(54) DOUBLE ENCODING DEVICE FOR INSIDE AND OUTSIDE CONTAINER ENCODING

(71) Applicant: Aesculap AG, Tuttlingen (DE)

(72) Inventors: Stephanie Auber, Tuttlingen (DE); Thomas-Erwin Kahler, Seitingen-Oberflacht (DE); Uwe Schaz, Neuhausen (DE); Roland-Alois Hoegerle, Tuttlingen (DE); Frederick Lenzenhuber, Tuttlingen (DE); Ralf Pfister, Trossingen (DE); Saul Dufoo Ochoa, Tuttlingen (DE); Simone Hermle, VS-Villingen (DE); Martin Machill, Rietheim-Weilheim (DE); André Buerk, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/283,592

(22) PCT Filed: Mar. 23, 2022

(86) PCT No.: PCT/EP2022/057616
§ 371 (c)(1),
(2) Date: Sep. 22, 2023

(87) PCT Pub. No.: WO2022/200419
PCT Pub. Date: Sep. 29, 2022

(65) Prior Publication Data
US 2024/0164867 A1 May 23, 2024

(30) Foreign Application Priority Data
Mar. 25, 2021 (DE) ..................... 10 2021 107 606.4

(51) Int. Cl.
*A61B 90/98* (2016.01)
*A61B 50/20* (2016.01)
(Continued)

(52) U.S. Cl.
CPC .............. *A61B 90/98* (2016.02); *A61B 50/20* (2016.02)

(58) Field of Classification Search
CPC ..................................................... A61B 90/98
See application file for complete search history.

(56) References Cited

U.S. PATENT DOCUMENTS

| 8,325,013 B2 | 12/2012 | Gerstel |
| 2005/0099292 A1 | 5/2005 | Sajkowsky |

(Continued)

FOREIGN PATENT DOCUMENTS

| CN | 110337654 A | 10/2019 |
| EP | 0630820 A1 | 12/1994 |

(Continued)

OTHER PUBLICATIONS

European Examination Report received in European Patent Application No. 22 714 458.1 dated Nov. 6, 2024, with translation, 6 pages.

(Continued)

*Primary Examiner* — Travis R Hunnings
*Assistant Examiner* — Pameshanand Mahase
(74) *Attorney, Agent, or Firm* — Christopher A. Rothe; CM Law

(57) ABSTRACT

A medical sterile goods container and a device setup for documenting a content and a location of the sterile goods container. The device setup includes the sterile goods container, a transport or storage device, and a holding device insertable into the sterile goods container. The sterile goods container has at least one first identification element that is (Continued)

identifiable by an identifier and able to be read digitally. The first identification element is located on an outside of the sterile goods container. The sterile goods container also has at least one second identification element that is identifiable by an identifier and able to be read digitally. The second identification element is located on an inside of the sterile goods container, with the identifier of the first identification element of the sterile goods container corresponding to the identifier of the second identification element of the sterile goods container.

14 Claims, 2 Drawing Sheets

(51) Int. Cl.

| | |
|---|---|
| *A61B 50/33* | (2016.01) |
| *A61B 50/34* | (2016.01) |
| *A61B 90/90* | (2016.01) |
| *G06Q 10/0832* | (2023.01) |
| *G06Q 10/0833* | (2023.01) |
| *G06Q 10/0875* | (2023.01) |

(56) References Cited

U.S. PATENT DOCUMENTS

| | | | |
|---|---|---|---|
| 2005/0258956 A1* | 11/2005 | Neuwirth | G06Q 10/087 |
| | | | 340/8.1 |
| 2006/0119481 A1 | 6/2006 | Tethrake et al. | |
| 2007/0094303 A1* | 4/2007 | Zwingenberger | G06Q 10/087 |
| 2008/0150722 A1 | 6/2008 | Jackson | |
| 2010/0063847 A1* | 3/2010 | Eisenberg | A61B 90/98 |
| | | | 705/332 |
| 2013/0063008 A1* | 3/2013 | Martin | G07F 9/06 |
| | | | 340/5.7 |

| | | | |
|---|---|---|---|
| 2015/0220764 A1 | 8/2015 | Pudenz et al. | |
| 2017/0224859 A1 | 8/2017 | Broninx et al. | |
| 2018/0015639 A1 | 1/2018 | Miyanaga | |
| 2019/0294942 A1 | 9/2019 | Sorli et al. | |
| 2019/0321132 A1 | 10/2019 | Weir et al. | |
| 2021/0084700 A1* | 3/2021 | Daniels | H04L 9/3226 |
| 2022/0096201 A1 | 3/2022 | Lenzenhuber | |
| 2023/0055196 A1* | 2/2023 | Zieris | A61B 90/90 |

FOREIGN PATENT DOCUMENTS

| | | | |
|---|---|---|---|
| EP | 2903086 A1 | 8/2015 | |
| EP | 3741248 A1 | 11/2020 | |
| JP | 2009077965 A | 4/2009 | |
| JP | 2010521725 A | 6/2010 | |
| JP | 2011204207 A | 10/2011 | |
| JP | 2017534429 A | 11/2017 | |
| JP | 2022519280 A | 3/2022 | |
| WO | 2005048041 A2 | 5/2005 | |
| WO | 2009003231 A1 | 1/2009 | |
| WO | 2015076746 A1 | 5/2015 | |

OTHER PUBLICATIONS

Search Report received in German Application No. 10 2021 107 606.4 dated Feb. 2, 2022, with translation, 14 pages.

Search Report received in International Application No. PCT/EP2022/057616 dated Jun. 27, 2022, with translation, 7 pages.

Written Opinion received in International Application No. PCT/EP2022/057616 dated Jun. 27, 2022, with translation, 14 pages.

Office Action received in Japanese Application No. 2023-558655 dated Aug. 29, 2025, with translation, 5 pages.

Office Action received in Chinese Application No. 202280024728.0 dated Apr. 23, 2026, with translation, 16 pages.

Search Report received in Chinese Application No. 202280024728.0 dated Apr. 16, 2026, with translation, 4 pages.

* cited by examiner

DOUBLE ENCODING DEVICE FOR INSIDE AND OUTSIDE CONTAINER ENCODING

CROSS-REFERENCE TO RELATED APPLICATIONS

This application is the United States national stage entry of International Application No. PCT/EP2022/057616, filed Mar. 23, 2022, and claims priority to German Application No. 10 2021 107 606.4, filed Mar. 25, 2021. The contents of International Application No. PCT/EP2022/057616 and German Application No. 10 2021 107 606.4 are incorporated by reference herein in their entireties.

FIELD

The present disclosure relates to a sterile goods container and a device setup for documenting a content and a location of a sterile goods container.

BACKGROUND

The requirements for documentation in medicine have increased significantly in recent years. Increasingly precise documentation of certain processes is required in medical facilities. This particularly affects the sterile goods cycle of medical products, such as surgical instruments, implants and the like.

The recording of the sterile goods cycle for medical products, devices, tools and the like is based in most cases on written documentation or checks at the end of the reprocessing cycle. The problem is that it is not possible to say with certainty how pre-cleaning, cleaning and disinfection, maintenance and sterilization were performed. Valid data are generated by handwritten notes, but this procedure is very error-prone. In hectic emergency situations, for example, the removal of a medical product from a sterile goods container may not be recorded manually, especially written by hand.

Furthermore, operating times of electric, pneumatic or hydraulic tools cannot be documented in relation to an individual tool. Another problem is the lack of identification of individual instruments and tools and the recording of their service life.

WO 2005 048 041 describes a container that is provided with an RFID element. The contents of the container and other relevant information are stored on this RFID element via a writing device. In a first embodiment, the contents are documented manually by a person when the container is filled and are stored on the RFID element. In another embodiment, the container is equipped with an RFID reader, which reads RFID elements provided on the contents (instruments, tools, etc.) of the container and then writes the information about which contents the container carries/stores on the RFID element of the container.

For the monitoring and traceability of sterile goods, it has to be possible to determine whether medical products or instruments have successfully undergone the entire reprocessing process and all necessary maintenance steps have been carried out. Sterile goods are stored and transported in designated holding devices in sterile goods containers.

As of today, it is not possible to say what holding device is in which sterile goods container without first having made a manual assignment via a packing plan and a subsequent manual container assignment. Furthermore, a sterile goods container cannot be found intuitively. Instead, it always has to be moved to its original location or provided with a manual identifier. In large shelves, this can mean an increased expenditure of time, among other things. In addition, such a manual assignment offers room for errors and uncertainties.

Sterile goods containers are transported on transport trolleys, referred to as medical trolleys. At present, it is not possible to determine the contents of these trolleys when the doors are closed. In addition, tracking or tracing (location tracking) of the medical trolley is not possible.

Alternatively, a manually created packing list can be viewed, whereby the products are usually listed there without a serial number, which makes the individual tracking of products impossible.

In addition, products can be removed from the sterile goods container during transport or storage. This may remain undetected. However, the previously removed product is needed at the latest when it is used in the operation. Completeness cannot be checked in advance without comparing the contents of the sterile goods container with a packing plan.

Furthermore, no automated, robot-assisted or autonomous operation of a reprocessing unit for medical products is possible.

SUMMARY

The object of the disclosure is therefore to avoid or at least reduce the disadvantages of the prior art. In particular, the documentation and the traceability of a content and a location of a sterile goods container is to be improved.

The medical sterile goods container comprises a holding device insertable into the sterile goods container in the form of a sieve basket or a perforated metal plate or a sterilization box configured for receiving medical products. According to the disclosure, the medical sterile goods container is provided with at least one digitally readable first identification element identifiable by an identifier on an outer side of the medical sterile goods container and with at least one digitally readable second identification element identifiable by an identifier on an inside of the medical sterile goods container. The identifier of the first identification element of the medical sterile goods container corresponds to the identifier of the second identification element of the sterile goods container.

In other words, at least the first identification element is attached to the outer side of the sterile goods container and at least the second identification element is attached to the inside of the sterile goods container, whereby all identification elements of the sterile goods container have an identical identifier. The first identification element and the second identification element are preferably RFID transponders. Other preferred embodiments of the first and second identification elements include an NFC element, a barcode, a sign, a color panel, a data matrix, and the like. The first and second identification elements are fixedly or detachably connected to the sterile goods container and enable identification of the sterile goods container.

In other words, the core of the invention is that the first identification element is located on the outer side of the sterile goods container and is provided and configured to be read by the (first) control unit arranged on the outside, preferably of a transport or storage device, via the (first) reading device arranged on the outside, and that the second identification element is located on the inside of the sterile goods container and is provided and configured to be read by the (second) control unit arranged on the inside, preferably of the holding device, via the (second) reading device arranged on the inside, wherein the identifier of the first identification element corresponds to the identifier of the second identification element.

The holding device, which is provided and configured for insertion into the medical sterile goods container, may have the reading device arranged on the inside. This reading device arranged on the inside enables the second identification element of the sterile goods container to be read. The reading device arranged on the inside may be connected to a control unit arranged on the inside located on the holding device, preferably via a cable. Furthermore, the control unit arranged on the inside is preferably connected wirelessly to the reading device arranged on the inside. The reading device arranged on the inside may preferably be an RFID reader. Other preferred embodiments include an NFC reader, a barcode reader (barcode scanner), a camera and the like, wherein the reading device arranged on the inside and the second identification element are compatible. In other words, the reading device is provided and adapted to read the identifier encoded/stored in the identification element. The holding device is preferably a sieve basket. Further preferred embodiments are a perforated metal plate, a sterilization box or devices specially configured for receiving medical products, which allow to fix and distance the medical product from adjacent medical products.

In another preferred embodiment, the control unit arranged on the inside may be provided and configured for determining, via reading the second identification element via the reading device arranged on the inside, in which medical sterile goods container the holding device is located, the holding device preferably being provided and configured for recognizing the medical products stored in/on it and for transmitting this information to the control unit arranged on the inside.

In other words, the control unit arranged on the inside of the holding device can identify the second identification element of the sterile goods container via the reading device arranged on the inside on the holding device when the holding device is located in the sterile goods container. For this purpose, the identifier stored in the second identification element is read out by the control unit arranged on the inside via the reading device arranged on the inside.

Preferably, the holding device may have sensors that detect which medical products or tools are stored in the holding device. For example, identification of the item numbers, serial numbers and recording of individual cycle numbers of the medical products or tools is possible. This can be done, for example, via individual product identifiers attached to the medical products, which can be read by the sensors of the holding device. In a preferred embodiment, these individual product identifiers of the medical products are RFID transponders. Other preferred embodiments include an NFC element, a barcode, a sign, a color chart, a data matrix, and the like.

The identification of the identifier of the second identification element enables the control unit arranged on the inside to make an unambiguous assignment of the holding device to the sterile goods container when the holding device is located in the sterile goods container.

In addition, the sensors of the holding device preferably detect which medical products are stored in the holding device. Overall, it is therefore possible to identify what medical products are in which sterile goods container without opening it. This prevents errors from occurring due to manual maintenance of packing lists and considerably speeds up the process of creating the packing list. In addition, manual packing lists usually only contain the item numbers of the medical products and do not contain serial numbers. The embodiment described here enables simple reading of the serial number of the medical products, which makes individual tracking possible.

Another advantage of the described embodiment is that it is detected when a medical product is removed from the sterile goods container. This enables a completeness check of a sterile goods container prepacked for an operation, for example, without opening it and possibly contaminating it.

The device setup for documentation of contents and a location of the medical sterile goods container includes the medical sterile goods container, a transport or storage device and a holding device insertable into the sterile goods container in the form of a sieve basket configured for receiving medical products or a perforated metal plate or a sterilization box.

The transport or storage device has at least one storage space for said sterile goods container, whereby there is preferably room for exactly one sterile goods container at a storage space. The transport or storage device is preferably a medical trolley with compartment bottoms. Further preferred embodiments are a shelf, a cabinet, a transport cart and the like. Outside the container, preferably at least the first reading device is arranged at each storage space. Preferably, the transport or storage device is a mobile device. Further preferably, the transport or storage device is an immobile device.

The transport or storage device is preferably provided with at least one storage space, which is provided with at least one reading device arranged on the outside, which is connected to a control unit arranged on the outside of the transport or storage device and is provided and configured to read the first identification element. The holding device, which is insertable into the sterile goods container, is provided with the control unit arranged on the inside and at least one reading device arranged on the inside, which is provided and configured to read the second identification element.

In the control unit arranged on the outside, each reading device arranged on the outside is linked to a storage device. This means that the control unit arranged on the outside saves the storage space to which the respective control unit arranged on the outside is attached. This reading device arranged on the outside enables the first identification element of the sterile goods container to be read. The reading device arranged on the outside is preferably an RFID reader. Other preferred embodiments include an NFC reader, a barcode reader (barcode scanner), a camera and the like, wherein the reading device arranged on the outside and the first identification element are compatible. In other words, the reading device arranged on the outside is provided and configured to read the identifier encoded/stored in the identification element. The reading device arranged on the outside is connected to a control unit arranged on the outside located at the transport or storage device preferably via a cable. Further preferable, the control unit arranged on the outside is preferably wirelessly connected to the reading device arranged on the outside.

In a first preferred embodiment, the control unit arranged on the outside is provided and configured to determine the storage space (local position) where the sterile goods container is located by reading the first identification element via the reading device arranged on the outside.

In other words, the control unit arranged on the outside identifies the first identification element of the sterile goods container via the reading device arranged on the outside provided on the storage space when the sterile goods container is located on the storage space. Preferably, the reading device arranged on the outside is located in a compartment bottom of the storage space. Further preferably, the reading device arranged on the outside is fixedly or removably disposed on an upper side or a lower side of the compartment bottom of the storage space. By reading the identifier of the first identification element of the sterile goods container, the control unit arranged on the outside recognizes which sterile goods container is located at the storage space. Preferably, each storage space is provided with a unique storage space identifier, which is stored in the control unit arranged on the outside and is assigned to the associated reading device arranged on the outside.

Further preferably, the storage space identifier also enables an unambiguous assignment to a transport or storage device. In other words, the storage space identifier indicates the transport or storage device in which the storage space is located.

Thus, when the sterile goods container is located on the storage space of the transport or storage device, the control unit arranged on the outside can recognize the first identification element of the sterile goods container via the reading device arranged on the outside and links the identifier of the first identification element of the sterile goods container with the storage space identifier of the storage space.

Reading out the identifier of the first identification element of the sterile goods container enables the sterile goods container to be unambiguously assigned to a storage space. This prevents errors from occurring due to manual maintenance of storage lists and considerably speeds up the process of creating storage lists. In addition, storage spaces can be updated automatically. If, for example, a sterile goods container is transferred from one storage space, for example in a rack, to another storage space, for example in a medical trolley, this can be automatically registered and updated by the control unit arranged on the outside on the rack and the control unit arranged on the outside on the medical trolley. In particular, the control unit arranged on the outside on the rack registers that the sterile goods container is no longer in the storage space of the rack and the control unit arranged on the outside on the medical trolley registers that the sterile goods container is in the storage space of the medical trolley. This prevents a sterile goods container from being moved in the event of a medical emergency, for example, without this being detected.

In other words, this enables tracking and tracing of the sterile goods container and, consequently, of the holding device and the medical products in the holding device.

In a further preferred embodiment, at least one control unit arranged on the outside and at least one control unit arranged on the inside are provided and configured to communicate with each other, with the communication preferably taking place directly.

In other words, the control unit arranged on the outside communicates the information determined by it via reading/identification of the first identification element via the reading device arranged on the outside, in particular the information as to which a sterile goods container is located in a storage space of the transport or storage device, to any number of control units arranged on the outside and on the inside. The control unit arranged on the inside communicates the information determined by it via reading/identification of the second identification element via the reading device arranged on the inside, in particular the information in which sterile goods container the holding device is located, to any number of control units arranged on the outside and on the inside.

Preferably, the inside control unit of the holding device additionally communicates the information about which medical products or tools are located in this holding device to any number of control units arranged on the outside and on the inside.

Communication is explicitly not limited to communication between control units arranged on the outside and control units arranged on the inside. A control unit arranged on the outside can also communicate with other control units arranged on the outside, and a control unit arranged on the inside can communicate with other control units arranged on the inside. As a result, the storage space of each sterile goods container and preferably its contents are stored in each control unit arranged on the outside and on the inside. This communication is preferably wireless, in particular preferably via Bluetooth, IEEE 802.11, mobile radio or the like.

Through communication between the control units arranged on the outside and on the inside, it is possible to obtain information from any of the control units arranged on the outside and on the inside as to which sterile goods container contains a holding device, which medical products are contained in this holding device, and at which storage space of the transport or storage device the sterile goods container is located. This facilitates the search for a specific sterile goods container or a specific medical product and enables tracking of individual medical products.

In another preferred embodiment, at least the one control unit arranged on the outside and at least the one control unit arranged on the inside are provided and configured to communicate with each other and to communicate with an external device.

In other words, the information read out by the control unit arranged on the outside as well as the information read out by the control unit arranged on the inside is preferably transmitted to an external device in addition to communication with each other. The external device is preferably an external computing and storage unit and in particular preferably a server. The external device is preferably integrated in a local network. Alternatively, the external device is integrated in a global network, such as the Internet. The information of the control units arranged on the outside and on the inside can be accessed via the external device. Preferably, the information can be accessed via a user interface, in particular via a web interface. Further preferably, access to this user interface is encrypted in order to prevent unauthorized access. Preferably, the user interface includes a search function, in particular a search function that allows to search specifically for the storage space of a sterile goods container or a medical product. Further preferably, the search function also allows direct entry of a storage space so that the contents of the sterile goods container stored there can be requested.

Preferably, the information is transmitted wirelessly to the external device, in particular via Bluetooth, via IEEE 802.11 or via mobile radio or the like.

Alternatively, the external device is preferably a handheld device. Preferably, the handheld device is a cell phone, in particular a smartphone, on which the information read out by the control unit arranged on the outside and the control unit arranged on the inside is displayed in an application provided for this purpose. Further preferably, the handheld device is a handheld device with a screen and operating elements, which is configured and intended to receive and display the information from the control unit arranged on the outside and the control unit arranged on the inside. Further preferably, the handheld device includes a search function, in particular a search function that allows a targeted search for the storage space of a sterile goods container or a medical product. Preferably, the search function also allows direct entry of a storage space so that the contents of the sterile goods container stored there can be requested.

By transmitting the information to an external device, it is possible to access the information from the control unit arranged on the outside and the control unit arranged on the inside quickly and from any location. This facilitates the search for a specific sterile goods container and/or a specific medical product. In addition, the content of a sterile goods container can be easily checked for completeness, for example on the way to the operating room. It is also possible to determine the length of time that the sterile goods container has been in the operating room before it reaches the medical product processing unit (AEMP).

In a further preferred embodiment, the control unit arranged on the outside is provided and configured to transmit the information received from the control units arranged on the outside and on the inside to the manufacturer of the medical products or an external service provider, so that the latter can offer life cycle management of the medical products.

In another preferred embodiment, the external device is provided and configured to store a copy of the information determined by the control unit arranged on the outside and the control unit arranged on the inside.

In other words, the information transmitted from the control unit arranged on the outside and the control unit arranged on the inside to the external device is copied, and the copy of the information is stored in a memory of the external device.

By storing a copy of the information that the control unit arranged on the outside and the control unit arranged on the inside transmit to the external device, it is possible to document and compare the cycle times of individual medical products. Furthermore, it is possible to document cycle numbers of individual medical products. This makes it possible to check whether a medical product has reached its prescribed maximum service life or whether maintenance is due. In addition, a copy of the information prevents loss of information in the event of a defect in a control unit arranged on the outside or on the inside.

In another preferred embodiment, the control unit arranged on the outside and the control unit arranged on the inside are provided and configured to connect to the external device and the control units arranged on the outside and control units arranged on the inside via at least one access point of a wireless connection.

In other words, the control unit arranged on the outside and the control unit arranged on the inside connect via an access point to the external device and further control units arranged on the outside and further control units arranged on the inside via a wireless connection. The wireless connection is preferably a radio technology, in particular Bluetooth, IEE 802.11 or the like. The access point is preferably a router, a repeater, an Access Point or the like. Preferably, several access points are available.

In yet other words, any number of control units arranged on the outside and on the inside can form a mesh and communicate with each other via a wireless connection. Optionally, the number of control units arranged on the outside and on the inside is variable.

The access points enable a wireless connection between the control units arranged on the outside and the control units arranged on the inside and the external device. This ensures that information can be exchanged between the control units arranged on the outside, the control units arranged on the inside and the external device even if individual control units arranged on the outside or on the inside are outside a transmission and reception range of further control units arranged on the outside or on the inside or the external device.

In a further preferred embodiment, the control unit arranged on the outside is provided and configured to determine its position in relation to the at least one access point via the signal strength of the wireless connection, preferably using more than one access point for the position determination.

In other words, the control unit arranged on the outside determines the signal strength of at least one wireless link to which it is connected and thereby determines at what location the control unit arranged on the outside is relative to the fixed position of the access point. The signal strength allows the control unit arranged on the outside to determine at what distance it is located relative to the access point. Preferably, the location is determined by triangulating several signal strengths and thus several distances to the fixed positions of the different access points. The fixed positions of the access points are preferably stored in the control unit arranged on the outside or in the external device, so that the control unit arranged on the outside can access the fixed positions of the access points.

By determining the location of the control unit arranged on the outside, it is possible to determine where a mobile transport or storage device is currently located relative to the fixed positions of the access points in an environment, such as a clinic. This facilitates tracking and searching for a transport or storage device.

In another preferred embodiment, the control unit arranged on the inside is provided and configured to determine its position relative to the at least one access point via the signal strength of the wireless link, preferably using more than one access point for position determination.

In other words, the control unit arranged on the inside determines the signal strength of at least one wireless link to which it is connected and thereby determines at what location the control unit arranged on the inside is relative to the fixed position of the access point. The signal strength allows the control unit inboard control unit to determine at what distance it is located relative to the access point. Preferably, the location is determined by triangulating several signal strengths and thus several distances to the fixed positions of the different access points. The fixed positions of the access points are preferably stored in the control unit arranged on the inside or in the external device, so that the control unit arranged on the inside can access the fixed positions of the access points.

By determining the location of the control unit arranged on the inside, it is possible to determine at which location a sterile goods container is currently located relative to the fixed positions of the access points in an environment, for example a clinic. Thus, it is possible to determine the storage location of a sterile goods container even if it is not located at a storage space of a transport or storage device provided with the reading device arranged on the outside and the control unit arranged on the outside.

DETAILED DESCRIPTION

Figure 1:
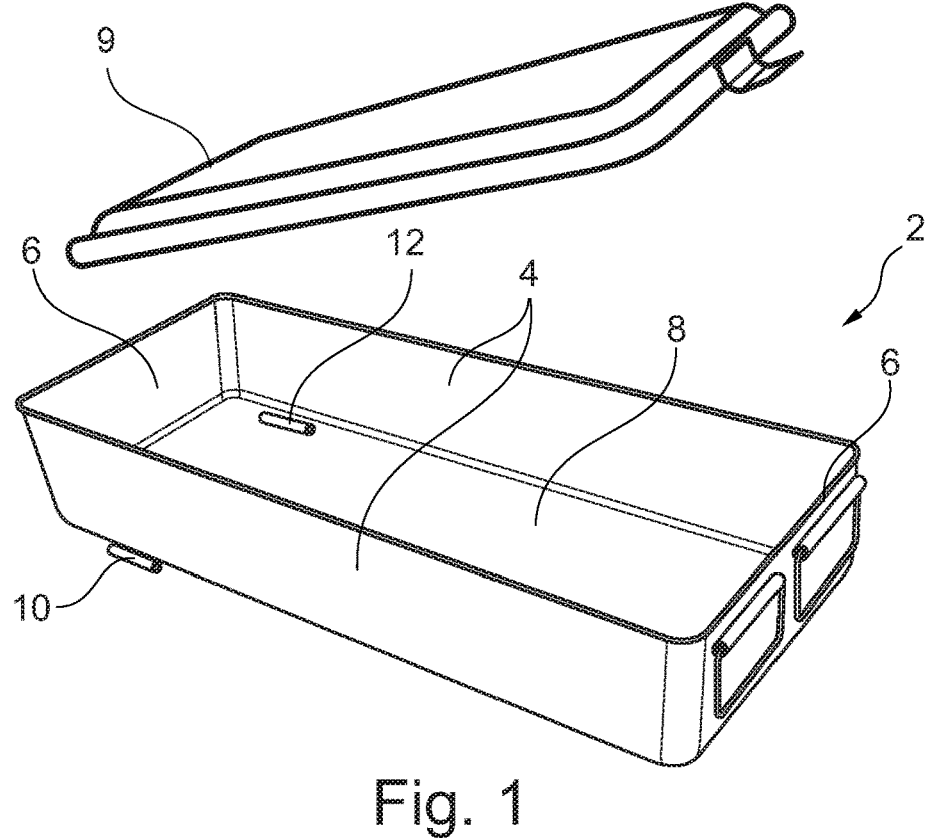
FIG. 1 is an illustration of a sterile goods container according to the disclosure with a first and a second identification element.

FIG. 1 shows a sterile goods container 2 with first sidewalls 4 and second sidewalls 6 and with a bottom 8 and a lid 9. The sterile goods container 2 is preferably made of aluminum. On an outer side of the sterile goods container 2, a first identification element 10 is firmly or detachably connected to the sterile goods container 2. The first identification element 10 is preferably an RFID transponder. Other preferred embodiments of the identification element include an NFC element, a barcode, a sign, a color panel, a data matrix, and the like. The outer side of the sterile goods container 2 comprises the outer sides of the first sidewalls 4, the outer sides of the second sidewalls 6 and the outer side of the bottom 8. On an inside of the sterile goods container 2, a second identification element 12 is fixedly or detachably connected to the sterile goods container 2. The second identification element 12 is preferably an RFID transponder. Other preferred embodiments of the identification element are an NFC element, a barcode, a sign, a color panel, a data matrix, and the like. The inside of the sterile goods container 2 consists of the inner sides of the first sidewalls 4, the inner sides of the second sidewalls 6 and the inner side of the bottom 8.

In a preferred embodiment, the lid 9 seals via a rubber seal on the opening edge of the sterile goods container 2. In another preferred embodiment, the opening edge has a fold which is used to seal the sterile goods container 2.

In a further preferred embodiment, the sterile goods container 2 has closures which are provided and configured to fix the lid 9 to the sterile goods container 2. Preferably, closures are located opposite each other on first sidewalls and/or on second sidewalls. Suitable closures include tension locks, twist locks, lever locks, electromechanical closures and the like.

In another preferred embodiment, a holder for a filter is provided in the lid 9 of the sterile goods container 2. Preferably, the holder for the filter has a centering pin. In yet another embodiment, the sterile goods container 2 has handles which are preferably provided with a silicone coating.

In yet another embodiment, the sterile goods container 2 is provided and configured to be stackable.

Figure 2:
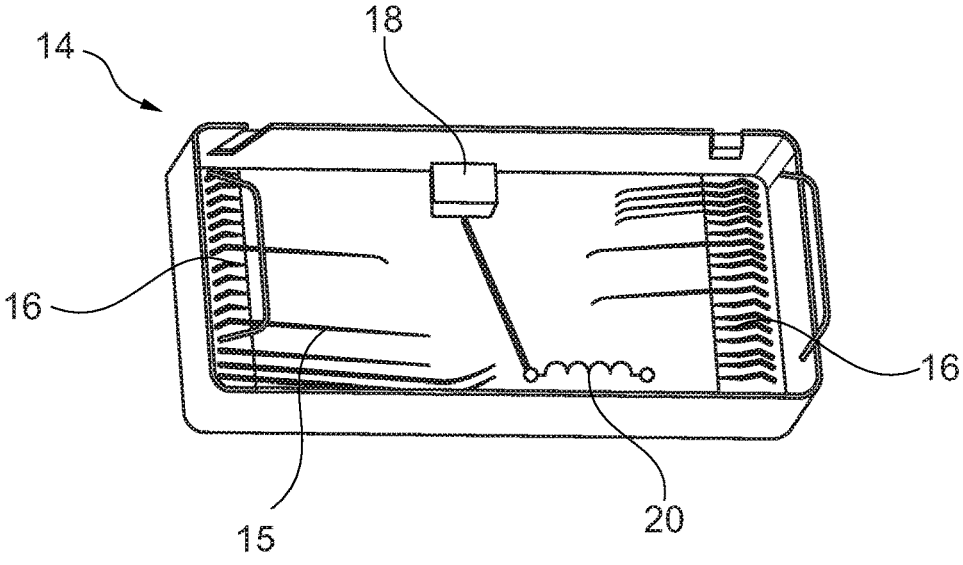
FIG. 2 is an illustration of a holding device according to the disclosure with receptacles for medical products.

FIG. 2 shows a holding device 14, which is provided and configured to hold medical products 15 and/or medical devices in a receptacle 16 provided and configured for this purpose and is also provided and configured to be inserted into the sterile goods container 2.

In a preferred embodiment, the holding device 14 is a sieve basket. Other preferred embodiments include a perforated metal plate, a sterilization tray, or a sterilization box. The receptacle 16 is provided and configured to receive and space apart medical products 15 from adjacent medical products 15. Preferably, the receptacle 16 is adapted to different medical products and has a sensor system with an energy storage and a data processing unit.

The sensor system of the receptacle 16 is preferably provided and configured to identify the medical products 15 in the holding device 14. For example, identification of the item numbers, serial numbers and individual cycle numbers of the medical products 15 is possible. This can be done, for example, via individual product identifiers attached to the medical products 15, which can be read by the sensors of the holding device 14. Further preferably, the receptacle 16 preferably has a data and antenna interface. The data and antenna interface is provided and configured to transmit the data determined by the sensor system of the receptacle 16.

The holding device 14 includes a second control unit (control unit arranged the inside) 18 and a second reading device (reading device arranged on the inside) 20 connected to the second control unit 18. The second reading device 20 is provided and configured to read the second identification element 12 of the sterile goods container 2. In a preferred embodiment, the second control unit 18 includes an energy storage, a data processing unit, a communication module and a reading module. The reading module preferably includes a multiplexer, which is provided and configured to address a plurality of second reading devices 20. In a preferred embodiment, the second reading device 20 is an antenna with a fixed number of conducting paths, which is connected to the second control unit 18 via the interfaces of the multiplexer.

Figure 3:
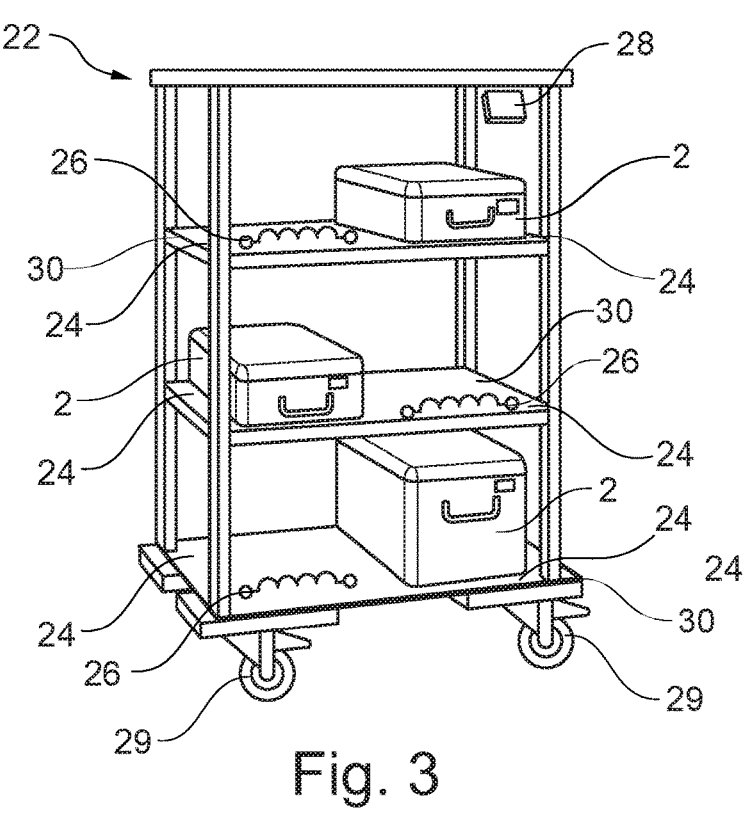
FIG. 3 is an illustration of a transport or storage device according to the disclosure with storage spaces for receiving sterile goods containers.

FIG. 3 shows a transport or storage device 22 with at least one storage space 24, which is provided and configured to receive a sterile goods container 2. The storage space 24 is equipped with at least one first reading device (reading device arranged on the outside) 26, which is provided and configured to read the first identification elements 10 on the outer side of the sterile goods container 2. The first reading device 26 is connected to a first control unit 28 (control unit arranged on the outside). The first control unit 28 includes an energy storage, a data processing unit, a communication module and a reading module. The reading module preferably includes a multiplexer, which is provided and configured to address a plurality of first reading devices 26. Preferably, the transport or storage device 22 is configured such that the storage space 24 is provided and adapted to receive exactly one sterile goods container 2.

In a preferred embodiment, the transport or storage device 22 is a medical trolley with wheels/rollers 29 which is equipped with individual compartment bottoms 30 on which the storage spaces 24 are provided. Preferably, the first reading device 26 is arranged in the compartment bottom 30. Further preferably, the first reading device is arranged on an upper side or on a lower side of the compartment bottom 30. In another preferred embodiment, the transport or storage device 22 is a stationary shelf-like storage device provided with individual compartment bottoms 30 on which the storage spaces 24 are provided.

Figure 4:
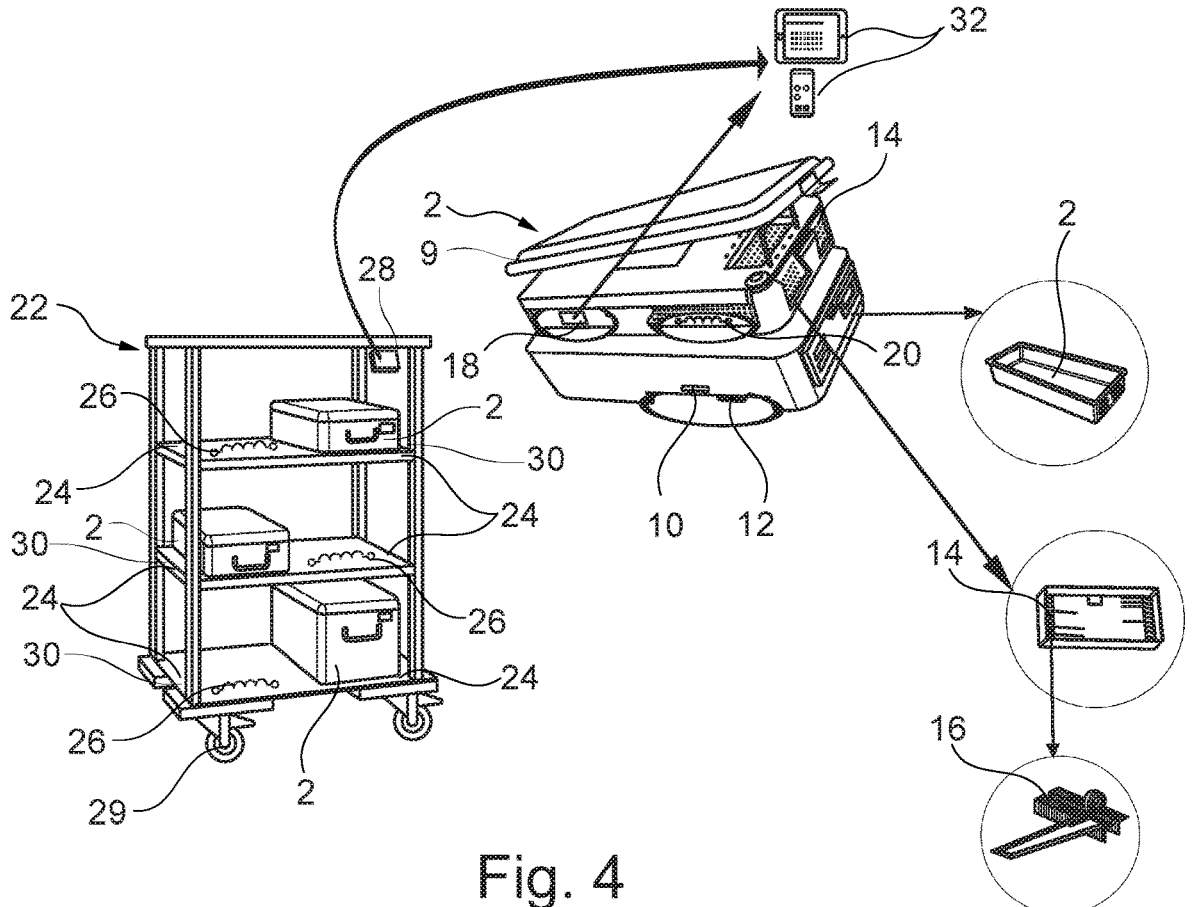
FIG. 4 is an illustration of a device setup according to the disclosure.

FIG. 4 shows a device setup with the sterile goods container 2, the transport or storage device 22 and the holding device 14 as well as the external device 32.

The transport or storage device 22 includes the at least one storage space 24 having at least one first reading device 26. Preferably, the storage space 24 is configured to receive a sterile goods container 2. Furthermore, the transport or storage device 22 includes the first control unit 28. The first control unit 28 includes an energy storage, a data processing unit, a communication module and a reading module. The reading module preferably includes a multiplexer, which is provided and configured to address a plurality of first reading devices 26. In a preferred embodiment, the first reading device 26 is an antenna having a predetermined number of conducting paths connected to the first control unit 28 via the interfaces of the multiplexer. The reading module of the first control unit 28 identifies, via the first reading device 26 provided at the storage space 24, the identifiers of the first identification element 10 of the sterile goods container 2 located at the storage space 24. The identifier of the recognized first identification element 10 is linked to the storage space identifier of the storage space 24 stored in the first control unit 28 or in the external device in the first control unit. The information obtained in this way, at which storage space 24 the sterile goods container 2 is located, is preferably communicated by the first control unit 28 directly to further first control unit 28 and to the second control unit 18 of the holding device 14 via the communication module of the first control unit 28, the communication preferably taking place wirelessly, in particular via Bluetooth, via IEE 802.11, via mobile radio or the like.

The second control unit 18 of the holding device 14 includes an energy storage, a data processing unit, a communication module and a reading module. The reading module of the second control unit 18 identifies the identifier of the second identification element 12 of the sterile goods container 2, in which the holding device 14 is located, via the reading device 26 provided on the holding device 14.

Preferably, the holding device 14 has sensors that detect which medical products are stored in the holding device 14. For example, it is possible to identify the item numbers, serial numbers and individual cycle numbers of the medical products. This can be done, for example, via individual product identifiers attached to the medical products, which can be read by the sensors of the holding device 14.

The medical products detected by the sensors of the holding device 14 are linked in the second control unit 18 with the identifier of the second identification element 12 of the sterile goods container 2. The information thus obtained as to what medical products are located in which sterile goods container 2 is communicated by the second control unit 18 preferably directly to the first control unit 28 of the storage and transport device 22 and to further second control units 18 of the holding device 14 via the communication module, the communication preferably being wireless, in particular via Bluetooth, via IEE 802.11, via mobile radio or the like.

In a preferred embodiment, the information read out by the first control unit 28, in particular at which storage space 24 of the transport or storage device 22 the sterile goods container 2 is located, is additionally transmitted to an external device 32, the transmission preferably being wireless, in particular via Bluetooth, via IEE 802.11, via mobile radio or the like. The information of the at least one first control unit 28 and the at least one second control unit 18 can be called up via the external device 32. Preferably, the information can be accessed via a user interface, in particular via a web interface. Further preferably, access to this user interface is encrypted in order to prevent unauthorized access. Preferably, the user interface includes a search function, in particular a search function that allows to search specifically for the storage space 24 of a sterile goods container 2 or a medical product. Preferably, the search function allows direct entry of a storage space 24 so that the contents of the sterile goods container 2 stored there can be requested.

The disclosure relates in summary to a device setup for documenting a content and a location of a sterile goods container comprising a sterile goods container, a transport or storage device and a holding device insertable into the sterile goods container. The sterile goods container is provided with at least one first identification element identifiable by an identifier and digitally readable on an outer side of the sterile goods container and with at least one second identification element identifiable by an identifier and digitally readable on an inside of the sterile goods container, wherein the identifier of the first identification element of the sterile goods container corresponds to the identifier of the second identification element of the sterile goods container. The transport or storage device comprises at least one storage space provided with at least one first reading device connected to a first control unit of the transport or storage device and is provided and configured to read a first identification element. The holding device insertable into the sterile goods container is provided with a second control unit and at least one second reading device, which is provided and configured to read a second identification element.

The invention claimed is:

1. A medical sterile goods assembly comprising:
   a medical sterile goods container comprising walls that collectively define an outer surface facing external to the medical sterile goods container and an inner surface facing an internal space of the medical sterile goods container;
   a holding device insertable into the internal space of the medical sterile goods container, the holding device comprising a sieve basket or a perforated metal plate or a sterilization box configured for receiving medical products;
   a first identification element that is digitally readable and identifiable by a first identifier located external to the medical sterile goods container; and
   a second identification element that is digitally readable and identifiable by a second identifier located within the internal space of the medical sterile goods container, wherein the first identifier corresponds to the second identifier, wherein the first identification element is attached to the outer surface of the walls of the medical sterile goods container and the second identification element is attached to the inner surface of the walls of the medical sterile goods container separately from the holding device.

2. The medical sterile goods assembly according to claim 1, wherein the holding device comprises a control unit arranged on an inside of the holding device and at least one reading device arranged on the inside of the holding device, wherein the at least one reading device is provided and configured to read out the second identification element.

3. The medical sterile goods assembly according to claim 2, wherein the control unit is configured to identify the medical sterile goods container in which the holding device is located by reading the second identification element with the at least one reading device.

4. The medical sterile goods assembly according to claim 2, wherein the holding device is configured for recognizing the medical products received in the holding device and for transmitting information regarding the medical products to the control unit.

5. A device setup for documentation of a content and a location of the medical sterile goods assembly according to claim 1, the device setup comprising:
   a transport or storage device having at least one storage space provided with at least one first reading device arranged on an outside of the transport or storage device and connected to a first control unit arranged on an outside of the transport or storage device, the at least one first reading device configured to read the first identification element.

6. The device setup according to claim 5, wherein the first control unit is configured to determine the at least one storage space where the medical sterile goods container is located by reading the first identification element via the at least one first reading device.

7. The device setup according to claim 5, further comprising a second control unit arranged on an inside of the transport or storage device, wherein the first control unit and the second control unit are configured to communicate with each other.

8. The device setup according to claim 5, further comprising a second control unit arranged on an inside of the transport or storage device, wherein the first control unit and the second control unit are configured to communicate with each other and to communicate with an external device.

9. The device setup according to claim 8, wherein the external device is configured to store a copy of information determined by the first control unit and the second control unit.

10. The device setup according to claim 8, wherein the first control unit and the second control unit are configured to connect to the external device via at least one access point of a wireless connection.

11. The device setup according to claim 10, wherein the first control unit is configured to determine a position of the first control unit relative to the at least one access point via a signal strength of the wireless connection.

12. The device setup according to claim 11, wherein the at least one access point comprises a plurality of access points.

13. The device setup according to claim 10, wherein the second control unit is configured to determine a position of the second control unit relative to the at least one access point via a signal strength of the wireless connection.

14. The device setup according to claim 13, wherein the at least one access point comprises a plurality of access points.

* * * * *